United States Patent [19]

Boaz

[11] Patent Number: 5,445,963
[45] Date of Patent: Aug. 29, 1995

[54] ALCOHOL-ESTER SEPARATION BY RECRYSTALLIZATION

[75] Inventor: Neil W. Boaz, Waterloo, N.Y.

[73] Assignee: Eastman Chemical Company, Kingsport, Tenn.

[21] Appl. No.: 660,830

[22] Filed: Feb. 26, 1991

Related U.S. Application Data

[63] Continuation-in-part of Ser. No. 501,570, Mar. 30, 1990, abandoned.

[51] Int. Cl.$^6$ ............................................. C12P 41/00
[52] U.S. Cl. ..................................... 435/280; 435/130; 435/157; 435/158; 435/814; 435/874; 435/876; 558/51; 558/52
[58] Field of Search ............... 435/280, 130, 157, 158; 558/51, 52; 434/874, 876, 814

[56] References Cited

U.S. PATENT DOCUMENTS

| | | | |
|---|---|---|---|
| 4,732,853 | 3/1988 | Whitesides et al. | 435/123 |
| 4,745,066 | 5/1988 | Hamaguchi et al. | 435/280 |
| 4,865,771 | 9/1989 | Francalanci et al. | 562/567 |
| 4,921,798 | 5/1990 | Boaz | 435/136 |
| 4,923,810 | 5/1990 | Walts et al. | 435/117 |

FOREIGN PATENT DOCUMENTS 189878  8/1987  European Pat. Off. ............ 435/130

OTHER PUBLICATIONS

Perry's Chemical Engineers' Handbook, 6th Ed. McGraw-Hill, pp. 17-3-17-12 (1984).

*Primary Examiner*—Shailendra Kumar
*Attorney, Agent, or Firm*—J. Frederick Thomsen

[57] ABSTRACT

A process is disclosed for the separation of an enantiomerically enriched 1-tosyloxy-2-acyloxy-3-butene and an enantiomerically enriched 1-tosyloxy-2-hydroxy-3-butene from a first mixture containing both compounds. The process includes the steps of:

(a) forming a solution of the mixture in an organic solvent;

(b) bringing the solution formed in (a) to a temperature wherein most of the enantiomerically enriched 1-tosyloxy-2-hydroxy-3-butene precipitates, leaving in solution most of the enantiomerically enriched 1-tosyloxy-2-acyloxy-3-butene; and (c) separating the precipitate formed in (b) from the solution.

8 Claims, No Drawings

ALCOHOL-ESTER SEPARATION BY RECRYSTALLIZATION

CROSS REFERENCE TO RELATED APPLICATIONS

The present application is a Continuation-in-Part of U.S. Ser. No. 501,570 filed 30 Mar. 1990, now abandoned entitled METHOD FOR THE PREPARATION OF OPTICALLY ACTIVE α,β-UNSATURATED EPOXIDES in the names of Boaz and Laumen. That parent application was abandoned as of the filing date accorded this application.

Reference is made to the following copending and commonly assigned applications, filed on even date herewith by Neil W. Boaz:

U.S. Ser. No. 660,838, entitled ALCOHOL-ESTER SEPARATION BY REACTION WITH BICARBONATE IN POLYHYDROXY SOLVENT, U.S. Ser. No. 660,839, entitled ALCOHOL-ESTER SEPARATION BY REACTION WITH ACETATE, and U.S. Ser. No. 660,837, entitled PROTECTED HYDROXY METHOD FOR ALCOHOL-ESTER SEPARATION.

FIELD OF THE INVENTION

The present invention relates to a process for producing enantiomerically enriched compounds from a mixture which can be derived from the enzymatic enantioselective hydrolysis of a racemic ester or the enzymatic enantioselective esterification of a racemic alcohol. The resulting enantiomerically enriched compounds find a number of uses as starting materials for other compounds. Some of the compounds are useful, for example, for the production of 2-deoxy-D-ribose. Other compounds are useful in the preparation of leukotrienes.

BACKGROUND OF THE INVENTION

Chemoenzymatic synthesis is a preparative strategy which employs both chemical and biocatalytic steps in a reaction sequence. The biocatalytic transformations convert one organic compound to another by the use of enzymes, either isolated or as part of biological systems. These biocatalysts (enzymes) are in principle the same as any other type of catalyst. However, there are circumstances where these biocatalysts are especially useful, such as the induction of chirality due to enzyme enantiospecificity. These enzymatic reactions occur under mild conditions and are often more environmentally acceptable than classical chemical processes.

Lipases are the closest to optimum biocatalysts. They are isolated extracellular enzymes whose natural function is to hydrolyze glycerol esters. Many have wide substrate acceptability for ester hydrolysis, or, under the correct conditions, alcohol esterification. They are readily (and often cheaply) available and are experimentally simple, requiring no added cofactors and affording no side products. Not surprisingly these enzymes have been the most thoroughly studied for biocatalytic use in organic chemistry.

There are two types of substrate classes for lipase-catalyzed reactions. Meso or prochiral substrates constitute the first and most widely-studied class. The inherent chirality of the lipase distinguishes between two prochiral functions (esters or alcohols) on the same molecule to afford 100% conversion to (optimally) a single enantiomer.

The second class of substrates are the racemic systems, in which (optimally) only one of two enantiomers is recognized and hydrolyzed (or esterified) by the lipase, affording a 50% conversion to product and 50% recovered starting material of opposite configurations. This mixture must be physically separated to complete the enantiomeric differentiation. For substrates in which the acid rather than the alcohol portion is of interest, the separation is often possible by simple aqueous base extraction.

Alcohol-based substrates pose the most challenging separation problems due to the gross physical similarity between the alcohol and ester. It is to separations of this type that the present invention is directed.

Chemoenzymatic synthesis of optically active epoxybutadiene (hereinafter EpB) is a potentially attractive preparative method since a readily available source of EpB has recently become available. Novel, simple, and efficient preparations of optically pure C4 synthons derived from EpB would be synthetically useful, since most currently available chiral synthons have a three- or five-carbon backbone due to availability from natural sources. In fact, chain elongation of C3 synthons from the chiral pool currently comprises the major method for the preparation of optically active EpB and the corresponding diol (1,2-dihydroxy-3-butene).

For example, an early route to S-1,2-dihydroxy-3-butene and S-EpB relied on C6 D-mannitol (two identical three-carbon pieces) as the chiral starting material. (Baer, E.; Fischer, H. O. L. J. Biol. Chem. 1939, 128, 463) After formation of the terminal (symmetrical) diacetonide, the vicinal diol was oxidatively cleaved with lead tetraacetate to provide two molecules of the unstable acetonide of the three-carbon synthon R-glyceraldehyde. Wittig reaction with methylene triphenylphosphorane afforded 1,2-dihydroxybutene acetonide which was readily deprotected to the optically active 1,2-dihydroxybutene. Monotosylation of the diol and base treatment afforded optically active EpB. (Crawford, R. J.; Lutener, S. B.; Cockcroft, R. D. Can. J. Chem. 1976, 54, 3364.)

The corresponding R enantiomers were available from the antipodal three carbon synthon S-glyceraldehyde acetonide which has been prepared from L-ascorbic acid by several routes. After initial differential protection of the hydroxyl groups by sequential actonide formation and methylation, ozonolysis and lithium aluminum hydride treatment afforded S,S-1,2,3,4-tetrahydroxybutane 1,2-acetonide. Lead tetraacetate oxidative cleavage resulted in the desired S-glyceraldehyde acetonide. This material can be transformed to optically active 1,2-dihydroxy-3-butene and ultimately to R-EpB.

Alternatively, optically active 1,2-dihydroxy-3-butene can be prepared from one of the few four carbon synthons available from the chiral pool, tartaric acid. After preparation of the acetonide and reduction of the carboxyl groups, formic acid-induced rearrangement and hydrolysis of the resulting formates afforded the desired diol. This can be transformed to optically active EpB.

All routes suffer from synthetic problems. The oxidation steps mentioned above can be troublesome and produce highly toxic (lead) by-products. The first two routes also involve a cumbersome Wittig olefination of glyceraldehyde acetonide, itself a rather unstable species. In addition, each of the two routes can only be utilized for a single (but complementary) enantiomer due to the commercial availability of only D-mannitol and L-ascorbic acid. The route from tartaric acid is complicated by the formation of 1,4-dihydroxy-2-butene during the rearrangement reaction. Separation of this isomer from the desired 1,2-dihydroxy-3-butene is not trivial.

In actuality, only the route from tartaric acid is directed towards C4 synthons. The other schemes afford C4 materials as an afterthought by chain extension. A more direct approach, the synthesis of optically active C4 synthons from corresponding racemic C4 starting materials, would afford greater versatility for the preparation of diverse organic molecules. Therefore, the preparation of optically active EpB and derivatives (from racemic EpB) using biocatalysis technology is of great interest. An enantioselective lipase-catalyzedhydrolytic approach to this problem seemed promising due to the presence of diverse oxygen functionalities in many EpB derivatives.

EpB can be converted to a racemic ester by a number of routes. This ester is then subjected to enzymatic enantioselective hydrolysis to produce a mixture of enantiomerically enriched alcohol and enantiomerically enriched ester. While these compounds can be separated using chromatographic separation techniques, this is not practical on a large scale. Unfortunately, as mentioned previously, the separation of the alcohol from the ester is difficult because of the similarity of the physical characteristics of these compounds.

Thus, the present invention is directed to the problem of separating an optically active alcohol from a related optically active ester.

SUMMARY OF THE INVENTION

A process is disclosed for the separation of an enantiomerically enriched 1-tosyloxy-2-acyloxy-3-butene and an enantiomerically enriched 1-tosyloxy-2-hydroxy-3-butene from a first mixture containing both compounds. The process includes the steps of:

(a) forming a solution of the mixture in a solvent, said solvent comprising an organic solvent;

(b) bringing the solution formed in (a) to a temperature wherein most of the enantiomerically enriched 1-tosyloxy-2-hydroxy-3-butene precipitates, leaving in solution most of the enantiomerically enriched 1-tosyloxy-2-acyloxy-3-butene; and (c) separating the precipitate formed in (b) from the solution.

The present invention is particularly advantageous since both of the enantiomerically enriched antipodes are recovered. Other methods recover one of the antipodes by destroying the other of the antipodes, thus reducing the overall yield of the process.

The invention is particularly useful in separating the alcohol and ester that are formed by the enzymatic enantioselective hydrolysis of a racemic acetate or the enzymatic enantioselective esterification of a racemic alcohol, with the racemic alcohol or acetate each in turn formed from 3,4-epoxy-1-butene. Thus, the invention is particularly useful for the separation of a mixture containing enantiomerically enriched 1-tosyloxy-2-hydroxy-3-butene and 1-tosyloxy-2-acyloxy-3-butene.

DETAILED DESCRIPTION OF THE INVENTION

In preferred embodiments, the mixture is represented by:

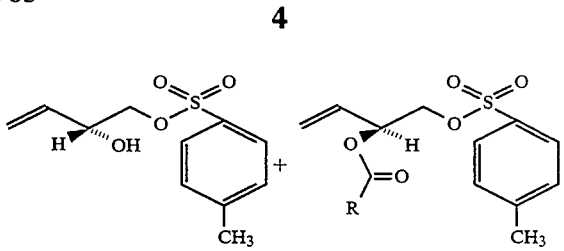

wherein R is a group selected from H, straight- or branched-chain substituted or unsubstituted alkyl, aryl, substituted aryl, arylalkyl, non-nitrogen-containing heteroaryl or substituted heteroaryl, or halogen. Substituents as designated above can be chosen from halogen, alkoxy, aryloxy, cyano, arylthio, alkylthio.

In accordance with the present process, a solution of the mixture to be separated is formed in an organic solvent. Useful organic solvents include dialkyl ethers, chlorinated hydrocarbons, esters of aliphatic acids, aromatic hydrocarbons, lower alcohols (C1–4) or mixtures thereof. Specific examples of polar solvents include toluene, diethyl ether, methanol, isopropanol and butyl acetate. Particularly useful solvents are either polar or aromatic solvents such as dialkyl ethers (polar) and toluene (aromatic).

In some instances, it is desirable to use, in addition to the above preferred solvents, a non-polar solvent to aid in the recrystallization. A non-polar solvent is particularly useful where the other solvent is toluene, diethyl ether or butyl acetate. Useful non-polar solvents include alphatic or alicyclic hydrocarbons or mixtures thereof. Specific examples of non-polar solvents useful in the invention include hexanes, heptane, pentane, and cyclohexane. The mixture is usually dissolved in the first solvent and then the optional non-polar solvent is added. Dissolution occurs at room temperature or with mild heating(e.g. to about 40° C.).

The ratio of the first to the non-polar solvent is not critical when a non-polar solvent is used. Usually the ratio is between about 5/1 and 0.2/1.

The currently preferred solvent is an about 1:1 mixture of toluene and heptane. Lower volumes of solvent are needed with this mixture. Further, toluene is preferred because of desirable physical characteristics, e.g. boiling point and flash point.

In the second step of the process, the solution is brought to a temperature wherein the hydroxy compound precipitates leaving in solution in the supernatant the acyloxy compound. This temperature is typically at or below room temperature. Preferred temperatures are in the range between about 25° C. and about −25° C. In the third step of the process, the precipitate is removed from the supernatant, such as by vacuum filtration.

During the recrystallization step, some of the hydroxy compound remains in the solution (the supernatant) with the acyloxy compound. This contaminant can be removed by one of the separation methods that consume hydroxy compounds to leave in solution the desired enantiomerically enriched acyloxy compound. Methods of this type include the methods described in the copending, commonly assigned applications mentioned above entitled: ALCOHOL-ESTER SEPARATION BY REACTION IN POLYHYDROXY SOLVENT and ALCOHOL-ESTER SEPARATION BY REACTION WITH ACETATE.

The recovered enantiomerically enriched acyloxy compound can be converted to the hydroxy compound by simple hydrolysis. Thus, the process of the invention can yield both optical configurations of the alcohol from the original mixture of, for example, an R-alcohol and S-ester. The R-alcohol precipitates from the solution while the S-alcohol can be easily prepared from the S-ester in the supernatant.

Either of the resulting hydroxy-tosylates can be purified by recrystallization to substantial optical purity.

Thus, the process of the invention can be illustrated, in its preferred embodiment, by the following reaction scheme:

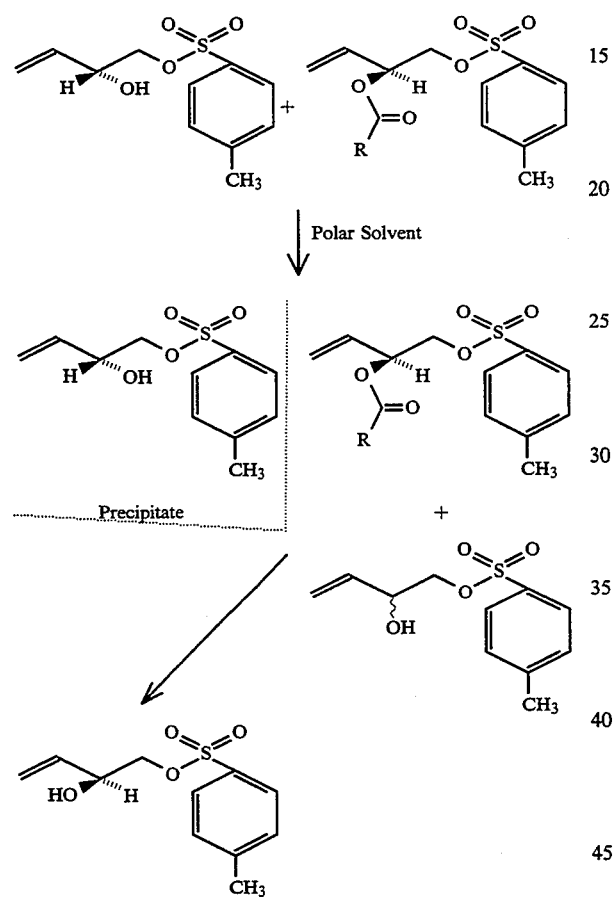

The invention relates to a method for the separation of an optically active alcohol from an optically active ester. The preparation of a typical mixture of this type will be discussed. In this process, EpB is first converted to a racemic acetate. This acetate is then subjected to enzymatic hydrolysis to produce the desired starting mixture. It will be understood, however, that the method of obtaining the desired mixture as well as the particular mixture itself is not critical to the invention in its broadest aspect. The described route is merely a preferred route.

A useful racemic ester starting substrate for enzymatic hydrolysis can be prepared from EpB by two routes. For efficiency, a tosylate group was chosen as the 1-alkoxy substituent to allow ready intramolecular displacement to form enantiomerically enriched EpB for further use. In addition, enzymatic hydrolysis of tosylated glycerol derivatives has been reported. (Hamaguchi, S.; Ohashi, T.; Watanabe, K. Agric. Biol. Chem. 1986, 50, 1629.) Groups other than tosylate can be used when other considerations become more important.

The 1-tosyloxy-2-acetoxy-3-butene substrate is also preferred since it can be hydrolyzed with high R-enantioselectivity by common lipases, affording a rapid route to optically active EpB.

The racemic acetate substrate was prepared by one of two methods. The diol route began with racemic 1,2-dihydroxy-3-butene which could be prepared by reacting EpB with water under neutral conditions or with acid catalysis. The diol was treated with p-toluenesulfonyl chloride (p-TsCl) in pyridine at 4° C. to afford the desired monotosylate contaminated with about 10% of the corresponding ditosylate. The monotosylate could be selectively crystallized to afford pure monotosylate in 61% yield. Hydroxy-tosylate was acetylated under normal conditions (Ac2O, Et3N, CH2Cl2) to provide the acetoxy-tosylate (the desired racemic acetate) in 93% yield. The diol route is illustrated as follows:

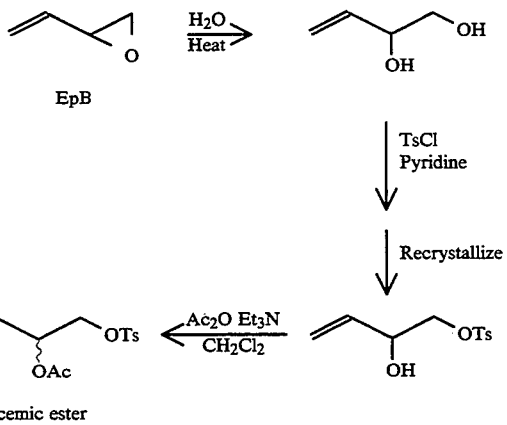

Racemic ester

Alternatively, the acetoxy-tosylate could be prepared by initial reaction of EpB with acetic acid under palladium(0) catalysis to afford 1-hydroxy-2-acetoxy-3-butene. Tosylation under normal conditions (p-TsCl, Et3N, CH2Cl2, 88%) afforded the desired product. However, the isomeric inconsistency of the monoacetate material (acetyl migration during distillative purification) and the inseparability of the positional isomers of two intermediates posed significant problems, since the unwanted isomers complicated the enzymatic hydrolysis. Therefore, the former (diol) preparation is preferred.

In the next step, the racemic ester was hydrolyzed in the presence of a lipase. (Convenient lipases are Lipase SAM-II ® derived from *Pseudomonas fluorescens* and Lipase PS-30 ® derived from *Pseudomonas cepacia*, both commercially available from Amano International Enzyme Company.)

The enzymatic enantioselective hydrolysis of the racemic ester proceeds using only a small amount (e.g., 50 mg crude lipase/0.1 mol racemic ester) of the lipase from *Pseudomonas fluorescens* or from *Pseudomonas capacia*. The reaction can be performed as an emulsion in aqueous pH 7 phosphate buffer under automatic titration conditions ("pH Stat", end point pH 7.00), allowing the reaction to be followed by the uptake of 1.000N NaOH. The reaction can be stopped at about 50% conversion, affording the R-enantiomer of the optically active alcohol and unreacted S-ester. The R-selectivity of the hydrolysis is very high, affording both enantiomers in high optical purity both >80% enantiomeric excess (ee)] with an R to S hydrolysis rate ratio (E value) of between 200 and 300. This is what is meant by "enantiomerically enriched". (The E value is determined in accordance with the methods described in (a) Chen, C. S.; Fujimoro, Y.; Girdaukas, G.; Sih, C. J. *J. Am. Chem. Soc.* 1982, 104, 7294. or (b) Chen, C. S.; Wu, S. H.; Girdaukas, G.; Sih, C. J. *J. Am. Chem, Soc.* 1987, 109, 2812.) In the same manner, "substantially optically pure" means >98% ee.

Alternatively, the lipase isolated from *Pseudomonas Novo* sp. ATCC 21808 can be used, affording the same configurational selectivity with an E value of upwards of 300.

A solution or well-dispersed emulsion is important for the success of an enzymatic hydrolysis reaction. In certain instances the mixture of optically active alcohol and optically active ester formed an undesirable gel prior to completion of the hydrolysis, halting the reaction early. A 9:1 pH 7 Buffer:tetrahydrofuran solvent mixture avoided this problem and also afforded a more rapid hydrolysis reaction (rate increased by a factor of 2) without sacrificing enantioselectivity (E values of up to 254 were observed). The enzymatic hydrolysis is illustrated as follows:

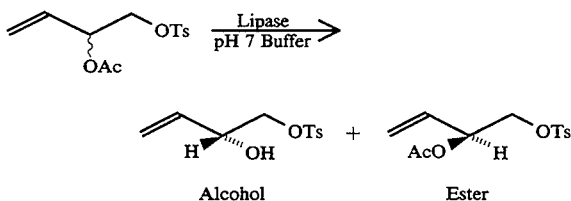

Substrate Preparation and Enzymatic Hydrolysis Diol Preparation Addition of Water to EpB EpB (250 g) was added to 800 mL of water, followed by 10 g of an acid resin. The reaction mixture was stirred at room temperature overnight. The catalyst was removed by filtration and the filtrate was concentrated at reduced pressure. Distillation of the residue (60°–65° C./1 mm) provided 3,4-dihydroxy-but-1-ene in 85% yield. $^1$H NMR (CDCl3): 5.9 (m, 1H); 5.4–5.2 (m, 2H); 4.25 (m 1H); 3.7 (m, 1H); 3.5 (m, 1H); 2.3 (br s, 1H). Ir(CCl4): 3600, 3499 (broad), 2900, 2880 cm$^{-1}$. Ms: 87, 70, 57, 42, 31, 29 m/e.

1-Tosyloxy-2-hydroxy-3-butene (Racemic Ester, diol route)

1,2-Dihydroxy-3-butene (20.00 g; 0.227 mol; 1.05 equiv) was dissolved in pyridine (200 mL). The reaction mixture was cooled in an ice bath and p-toluenesulfonyl chloride (p-TsCl) (41.11 g; 0.216 mol) was added in four portions over 30 min. After thorough mixing, the reaction mixture was placed at 4° C. for 18 h, at which time thin layer chromotography (hereinafter TLC) analysis indicated no p-TsCl. The mixture was concentrated to about half the original volume at reduced pressure from a 40° C. water bath and then diluted with ether (200 mL). The mixture was washed with water (100 mL), ice-cold 3N HCl until the washes remained acidic (2×100 mL), and saturated sodium bicarbonate (100 mL). After drying the organic solution (MgSO4), the solvent was removed to afford 41.73 g of a 91:9 mixture ($^1$H nmr analysis) of the desired compound and the corresponding di-tosylate. The crude product solidified over several days at −20° C. It was recrystallized from methylene chloride (50 mL) by the addition of hexanes (100 mL) and chilling to −20° C. to afford two crops (total 33.33 g; 61%) of the desired compound which was pure by TLC analysis, mp 38°–44° C. $^1$H nmr (300 MHz, CDCl3): 7.800 (2H, d, J=8.25 Hz); 7.356 (2H, d, J=8.19 Hz); 5.751 (1H, ddd, J=5.38, 10.46, 16.55 Hz); 5.378 (1H, br d, J=17.05 Hz); 5.247 (1H, br d, J=10.48 Hz); 4,396 (1H, m); 4.066 (1H, dd, J=3.39, 10.20 Hz); 3.906 (1H, dd, J=7.41, 10.22 Hz); 2.451 (3H, s); 2.276 (1H, d, J=4.50 Hz). IR (KBr, cm$^{-1}$): 3520 (s,b); 1650 (w); 1600 (s); 1350 (s); 1170 (s). Combustion Analysis: Theor—C, 54.53; H,5.82; N, 0. Found—C, 54.84; H, 5.86; N, <0.3.

1-Tosyloxy-2-acetoxy-3-butene

Tosylate from above (25.00 g; 0.103 mol) was dissolved in methylene chloride (125 mL) and cooled to 0° C. Triethylamine (21.5 mL; 0.155 mol; 1.5 equiv) was added followed dropwise by acetic anhydride (11.7 mL; 0.124 mol; 1.2 equiv). The reaction mixture was allowed to warm to room temperature and after 2.5 days no starting tosylate was visible by TLC analysis. The mixture was poured into ether (250 mL), washed with water (2×50 mL) and saturated sodium bicarbonate (50 mL), dried (MgSO4), and concentrated. The crude product was stirred with pH 7 phosphate buffer (100 mL) for 1.5 h to hydrolyze any excess acetic anhydride and extracted with ether (3×50 mL). The combined ether extracts were dried (MgSO4) and concentrated to afford 27.51 g (93%) of acetate product. $^1$H nmr (300 MHz, CDCl3): 7.786 (2H, d,J=8.26 Hz); 7.355 (2H, d, J=8.03 Hz); 5.710 (1H, ddd, J=6.23, 10.54, 17.05 Hz); 5.396 (1H, m); 5.324 (1H, d, J=16.72 Hz); 5,279 (1H, d, J=10.63 Hz); 4.09 (2H, m); 2.453 (3H, s); 2.017 (3H, s). IR (neat film, cm$^{-1}$): 1740 (s); 1645 (w); 1600 (m); 1360 (s); 1175 (s).

Optically active R-(+)-alcohol ([α]D$^{20}$ +7.14°(c. 1.036, methanol)) afforded R-(+)-ester, [α]D$^{20}$ +5.30° (c. 1.246, methanol), by this methodology.

Enzymatic Enantioselective Hydrolysis of Racemic Ester using SAM-II

Racemic ester described above (25.76 g; 90.6 mmol) and pH 7 phosphate buffer (90 g) were combined and vigorously stirred under pH Stat conditions (automatic titration—pH 7.00 end point). Once the pH had stabilized at 7.00, the lipase from *Pseudomonas fluorescens* (SAM II) (50 mg) was added. The mixture was stirred for 15 h under pH Star conditions at which time 45.54 mL of 1.000 N NaOH had been consumed. The mixture was extracted with methylene chloride (3×100 mL), dried (Na2SO4), and concentrated to afford 23.47 g (98% material recovery) of the mixture of alcohol and ester. A portion (about 350 mg) was flash chromatographed (elution with 1:2 ethyl acetate:hexanes) to afford R-alcohol (148 mg; 92% ee) and S-ester (195 mg; 94% ee). Enantiomeric excess was determined using a method analogous to that described in Dale et al, *J. Org. Chem.*, 1969, Vol 33, p2543.

R-alcohol: [α]D$^{20}$ +7.14° (c. 1.036, methanol)

S-ester: [α]D$^{20}$ −5.29° (c. 1.324, methanol).

All other properties are as described above for the alcohol and the ester.

Enzymatic Enantioselective Hydrolysis of Racemic Ester using the lipase from *Pseudomonas Novo* Sp. ATCC 21808

Racemic ester prepared as above (1.42 g; 5.00 mmol) and pH 7 phosphate buffer (20 g) were combined and vigorously stirred under pH Stat (automatic titration—pH 7.00 end point) conditions. Once the pH had stabilized at 7.00, an ammonium sulfate suspension of the lipase from Pseudomonas novo Sp. ATCC 21808 (1.00 mL) was added. The mixture was stirred for 4 h under pH Stat conditions at which time 2.471 mL of 1.000N NaOH had been consumed (49.4 % conversion). The mixture was extracted with methylene chloride (3×20 mL), dried (MgSO4), and concentrated. The crude product was flash chromatographed using 3:1 hexanes:ethyl acetate as eluent to afford 670 mg (47%; 92% ee) of S-ester and 447 mg (37%; 98% ee) of R-alcohol (one overlap fraction). Enantiomeric excess was determined using a method analogous to that described in Dale et al, J. Org. Chem., 1969, Vol 33, p2543.

R-alcohol: $[\alpha]D^{20}$ +7.14° (c. 1.036, methanol)

S-ester: $[\alpha]D^{20}$ −5.29° (c. 1.324, methanol).

All properties of the alcohol and the ester are as reported above.

Reduction of the olefin of the R-alcohol afforded the corresponding (−)-1,2-butanediol monotosylate. This compound is known to possess the R-(−) configuration (Hamaguchi, et al, Agri. Biol. Chem. vol 50, pg 1629 (1986).

The following examples are submitted for a further understanding of the invention:

EXAMPLE 1

Recrystallative Separation of 1-tosyloxy-2-acetoxy-3-butene and 1-tosyloxy-2-hydroxy-3-butene using Ether and Hexane An approximately 1:1 mixture of R-1-tosyloxy-2-hydroxy-3-butene (92% ee) and S-1-tosyloxy-2-acetoxy-3-butene (82% ee) (1118.3 g; combined 4.63 mol maximum) was dissolved in warm diethyl ether (1 L) and diluted with hexanes (1 L). Phase separation and precipitation was prompted by chilling the mixture to −20° C. for 2 days. This afforded 513.5 g of a solid which was composed of the hydroxy compound and the acetoxy compound in a ratio of 86:14 by $^1$H nmr analysis. The solid was dissolved in warm ether (1 L), diluted with hexanes (1.5 L) and chilled to −20° C. for 1.5 days to afford 424.1 g (38% yield from racemic esters) of enantiomerically enriched 1-tosyloxy-2-hydroxy-3-butene. No residual ester was detected by $^1$H nmr and thin layer chromotography (tlc) analysis.

The combined mother liquors were concentrated to afford 684.4 g of a mixture of acetoxy compound and hydroxy compound (73:27, respectively, by $^1$H nmr analysis). All properties of the alcohol and the ester are as previously reported.

Destruction of Residual Racemic alcohol Using (Tetramethylammonium Acetate)

The 73:27 mixture of S-ester and alcohol from the recrystallization mother liquors (10.00 g; 37.3 mmol total, 27.2 mmol ester and 10.1 mmol alcohol was dissolved in acetone (50 mL). Tetramethylammmonium acetate (3.36 g; 25.25 mmol; 2.5 equiv based on alcohol) was added, and the reaction mixture was stirred overnight at room temperature to completely consume the alcohol as determined by tlc analysis. The reaction mixture was diluted with ether (100 mL), washed with water (3×25 mL), dried (MgSO4), and concentrated to afford 7.64 g of crude S-ester. All properties of S-ester are as reported above.

Optically Pure Hydroxy-tosylate

The crude S-ester (7.64 g; 27.2 mmol maximum) from the previous reaction was dissolved in methanol (35 mL) and 3.5 mL concentrated hydrochloric acid was added. The reaction mixture was stirred at room temperature for 2.5 days to completely consume the ester as determined by tlc analysis. The reaction mixture was diluted with ether (70 mL), washed with saturated sodium bicarbonate (3×25 mL), dried (MgSO4), and concentrated to afford 5.10 g of crude S-alcohol, about 82% ee. This was recrystallized from warm ether (2.5 mL/g) by the addition of hexanes (5 mL/g) until substantial optical purity (>99% ee) was reached (two recrystallizations), affording 4.10 g (25% yield from the racemic ester). All properties of S-alcohol are as reported above.

Thus, the process of the invention yielded the R-alcohol from the precipitate and the S-alcohol from the supernatant.

Destruction of Residual alcohol using Potassium Bicarbonate

The 73:27 mixture of S-ester and alcohol from the recrystallization mother liquors (10.07 g; 37.5 mmol total, 27.4 mmol ester and 10.1 mmol alcohol was dissolved in ethylene glycol (37.5 mL). Potassium bicarbonate (5.05 g; 50.5 mmol; ester equiv based on alcohol was added and the reaction mixture was vigorously stirred overnight (14 h) at room temperature to completely consume the alcohol as determined by tlc analysis. This mixture was diluted with water (40 mL), extracted with ether (3×30 mL), dried (MgSO4), and concentrated to afford 8.17 g of crude S-ester which was utilized without further purification.

Optically Pure S-Hydroxy-Tosylate

Crude S-ester (8.17 g; 27.4 mmol maximum) was dissolved in methanol (40 mL) and concentrated hydrochloric acid (4 mL) was added. The resulting solution was stirred at room temperature for 24 h to completely consume ester as determined by tlc analysis. The reaction mixture was carefully diluted with saturated sodium bicarbonate (40 mL) to neutralize the HCl and extracted with ether (3×20 mL). The combined extracts were dried (MgSO4) and concentrated to afford 6.29 g of S-alcohol, about 82% ee. This material was recrystallized three times from warm ether (2.5 mL/g) by hexanes addition (5 mL/g) until substantial optical purity (>99% ee) was achieved (4.68 g; 29% yield from racemic esters). All properties of the S-alcohol are as reported above.

EXAMPLE 2

Recrystallative Separation of 1-tosyloxy-2-acetoxy-3-butene and 1-tosyloxy-2-hydroxy-3-butene using Toluene and Heptane An approximately 1:1 mixture of S-1-tosyloxy-2-hydroxy-3-butene (>95% ee) and R-1-tosyloxy-2-acetoxy-3-butene (>95% ee) (185.55 g; combined 0.70 mol maximum) was dissolved in toluene (85 mL; 1 mL/g of hydroxy-tosylate) at room temperature. Heptane (85 mL; 1 volume) was added with vigorous stirring. The mixture was stirred at room temperature for 30 min at which time crystallization had begun. The mixture was cooled to 4° C. overnight (no stirring) and the precipitate was collected and washed with cold toluene to afford 61.41 g (36%) of hydroxy compound contaminated with about 1% acetate. Recrystallization of this material from warm (about 40° C. toluene (122 mL; 2 mL/g) by chilling to 4° C. afforded 53.13 g (31%) of substantially optically pure S-hydroxy-tosylate free of any acetate compound by $^1$H nmr and tlc analysis.

Concentration of the initial mother liquors afforded 123.97 g of about 75:25 ratio of acetate to hydroxy compounds. Pure acetate could be obtained as described above in Example 1.

The present invention has been described with reference to particularly preferred embodiments thereof. However, it will be understood that modifications and extensions can be effected within the spirit and scope of the invention.

We claim:

1. A process for the separation of an enantiomerically enriched 1-tosyloxy-2-acyloxy-3-butene and an enantiomerically enriched 1-tosyloxy-2-hydroxy-3-butene from a first mixture containing both compounds, said process including the steps of:
   (a) forming a solution of said mixture in an organic solvent;
   (b) bringing the solution formed in (a) to a temperature wherein most of the enantiomerically enriched 1-tosyloxy-2-hydroxy-3-butene precipitates, leaving in solution most of the enantiomerically enriched 1-tosyloxy-2-acyloxy-3-butene; and
   (c) separating the precipitate formed in (b) from said solution.

2. The process according to claim 1 wherein said solvent comprises a mixture of a polar and a non-polar solvent.

3. The process according to claim 2 wherein the ratio of polar to non-polar solvent is between about 5/1 and 0.2/1.

4. The process according to claim 1 wherein said mixture is represented by the structures:

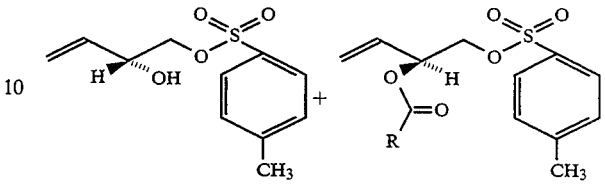

wherein R is a group selected from H, straight- or branched-chain substituted or unsubstituted alkyl, aryl, substituted aryl, arylalkyl, non-nitrogen-containing heteroaryl or substituted heteroaryl.

5. A process according to claim 4 wherein said firs mixture is produced by the enzymatic enantioselective hydrolysis of a racemic ester.

6. The process according to claim 5 wherein said racemic ester is derived from epoxybutadiene.

7. The process according to claim 1 wherein said organic solvent is a mixture of diethyl ether and hexane.

8. The process according to claim 1 wherein said solvent is a toluene/heptane mixture at a ratio of about 1/1.

* * * * *